United States Patent [19]

Marlinghaus

[11] Patent Number: 5,788,496
[45] Date of Patent: Aug. 4, 1998

[54] METHOD AND APPARATUS FOR TREATING TEETH

[75] Inventor: Ernst H. Marlinghaus, Bottighofen, Switzerland

[73] Assignee: Storz Medical AG, Kreuzlingen, Switzerland

[21] Appl. No.: 592,708

[22] Filed: Jan. 26, 1996

[30] Foreign Application Priority Data

Jan. 26, 1995 [DE] Germany ............... 195 02 277.7

[51] Int. Cl.$^6$ .............. A61C 3/03; A61B 17/22; B06B 3/04; G10K 11/18
[52] U.S. Cl. .............. 433/215; 433/299; 601/4; 606/128
[58] Field of Search .............. 433/86, 150, 215, 433/229; 604/22; 606/127, 128; 601/4

[56] References Cited

U.S. PATENT DOCUMENTS

| | | | |
|---|---|---|---|
| 2,874,470 | 2/1959 | Richards | 433/86 |
| 3,076,904 | 2/1963 | Kleesattel et al. | 433/86 |
| 3,091,033 | 5/1963 | Ellman | 433/86 |
| 3,332,150 | 7/1967 | Mumaw | 433/215 |
| 4,127,125 | 11/1978 | Takemoto et al. | 433/86 |
| 4,144,646 | 3/1979 | Takemoto et al. | 433/119 |
| 4,248,232 | 2/1981 | Engelbrecht et al. | 433/86 |
| 4,637,256 | 1/1987 | Sugiyama et al. | 433/215 |
| 4,901,709 | 2/1990 | Rattner | 606/128 |
| 4,928,672 | 5/1990 | Grasser et al. | 606/128 |
| 5,106,302 | 4/1992 | Farzin-Nia et al. | 433/215 |

FOREIGN PATENT DOCUMENTS 38 35 318   6/1990   Germany.

*Primary Examiner*—Ralph Lewis
*Attorney, Agent, or Firm*—Evenson, McKeown, Edwards & Lenahan P.L.L.C.

[57] ABSTRACT

A method is described for removing tooth fillings and shattering teeth using a device that generates focused acoustic pressure or shock waves with an appropriate energy. The focussed waves are coupled into the tooth and/or the filling. The apparatus includes a sound generating unit for generating focussed pressure or sound waves and a coupling cushion for coupling the focussed waves through a cheek or open mouth of the patient into the tooth or filling to be removed.

5 Claims, 1 Drawing Sheet

5,788,496

1

METHOD AND APPARATUS FOR TREATING TEETH

BACKGROUND AND SUMMARY OF THE INVENTION

The invention relates to a method and an apparatus for treating teeth.

In the past, amalgam has very frequently been used for filling cavities in teeth. For some time, however, it has been suspected that amalgam is responsible for a number of diseases, in addition to which it could even cause cancer. As a result, many patients now request that their old amalgam fillings be removed.

When the amalgam filling is drilled out, dust develops. With water irrigation used during the drilling, some of the dust can be swallowed by the patient. Hence there is a great need to remove tooth fillings, particularly amalgam fillings, with the least possible degree of dust development.

A further problem arises when teeth are "pulled," particularly wisdom teeth. For one thing, tooth extraction requires considerable expenditure of time and force and is bloody—a non-negligible problem in the age of AIDS. For another, wisdom teeth are often very "grown in" so that they cannot be pulled without first being broken. It is readily apparent that this is an extremely painful procedure for the patient.

The invention therefore relates to a method and an apparatus for treating teeth, particularly for removing fillings as well as the tooth itself, whereby fillings can be removed without dust developing and teeth can be removed without direct contact and with minimal bleeding.

The present invention meets these needs by providing a method for removing tooth fillings using a device which generates focussed acoustic pressure or shock waves at an appropriate energy level. The focussed waves are coupled into the tooth and/or the filling. The method can further be used to shatter teeth, particularly wisdom teeth, wherein the focussed acoustic pressure or shock waves at an appropriate energy level are coupled into the wisdom tooth.

The present invention further provides an apparatus for carrying out the method. The apparatus includes a sound generating unit for generating focussed pressure or sound waves and a coupling cushion which couples the focussed waves through the cheek or mouth into the tooth or filling to be removed.

In the method according to the invention, a device is used which generates focused acoustic pressure and/or shock waves with appropriate energy. The focused waves are coupled into the tooth and/or the filling.

By coupling the shock and/or pressure waves into the tooth or filling, the connection between the filling and the tooth is destroyed, so that in most cases the filling, consisting for example of amalgam, can be removed as a whole. Also, even when the filling is destroyed, the resulting fragments are so large that they can be easily removed or suctioned off without dust developing or without running the risk of the patient swallowing the fragments.

One method according to the invention for removing teeth, particularly wisdom teeth, differs from the above-described method for removing fillings essentially only by the amount of energy coupled-in. Removal of the tooth in question is accomplished by this tooth being destroyed or shattered. The fragments can then easily be removed in the conventional manner. For destroying or shattering teeth, and in particular wisdom teeth, all that is needed is considerably more energy than is otherwise required for removing fillings.

2

Provision of the necessary energy is not a problem, however, with devices known from other fields for generating focused pressure or shock waves, for example the known lithotriptors.

In both cases however, the pain sensation experienced by the patient is astonishingly slight.

In a preferred embodiment of the present invention, the focused waves are coupled in through the cheek. It is especially preferred that a coupling cushion be disposed between the cheek and the tooth. Through the use of the coupling cushion, optimum energy conduction between the cheek, which the sound generating unit abuts possibly with another coupling cushion in between, and the tooth to be treated is ensured.

In another preferred embodiment, the device for generating focused acoustic waves or a coupling cushion of the device is brought into contact with the tooth or the filling through the open mouth.

The device for carrying out the method according to the present invention has a sound-generating unit, which generates focused acoustic pressure or sound waves, and a coupling cushion which couples in the focused waves through the cheek and/or the open mouth into the tooth or the filling to be removed.

The sound generating unit can be a sound pulse generating unit, as is known in a similar manner for shattering stones, particularly kidney and gallbladder stones. A device suitable for use as a sound pulse generating unit is disclosed in German Patent document DE 38 35 318 C1, the disclosure of which is hereby expressly incorporated by reference for all of the technical features not described in detail in this application. Of course any other sound generating unit can be used, in the manner of a lithotriptor.

In particular, the sound generating unit can have an electromagnetic, magnetostrictive, or piezoelectric pressure wave generator or a shock wave unit with electrodes or an explosive unit.

The pressure wave generator or shock wave unit can generate waves that are already focused. The pressure wave generator can, for example, have the shape of a dome.

Of course, it is possible however for a reflector or an acoustic lens to focus the waves generated by the pressure wave generator or shock wave unit.

Other objects, advantages and novel features of the present invention will become apparent from the following detailed description of the invention when considered in conjunction with the accompanying drawings.

DETAILED DESCRIPTION OF THE DRAWING

Figure 1A:
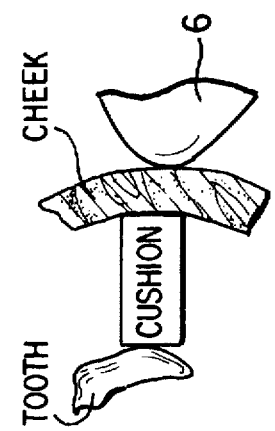
FIG. 1 is a partial cross-sectional view of an apparatus for treating teeth according to the present invention.
Figure 1:
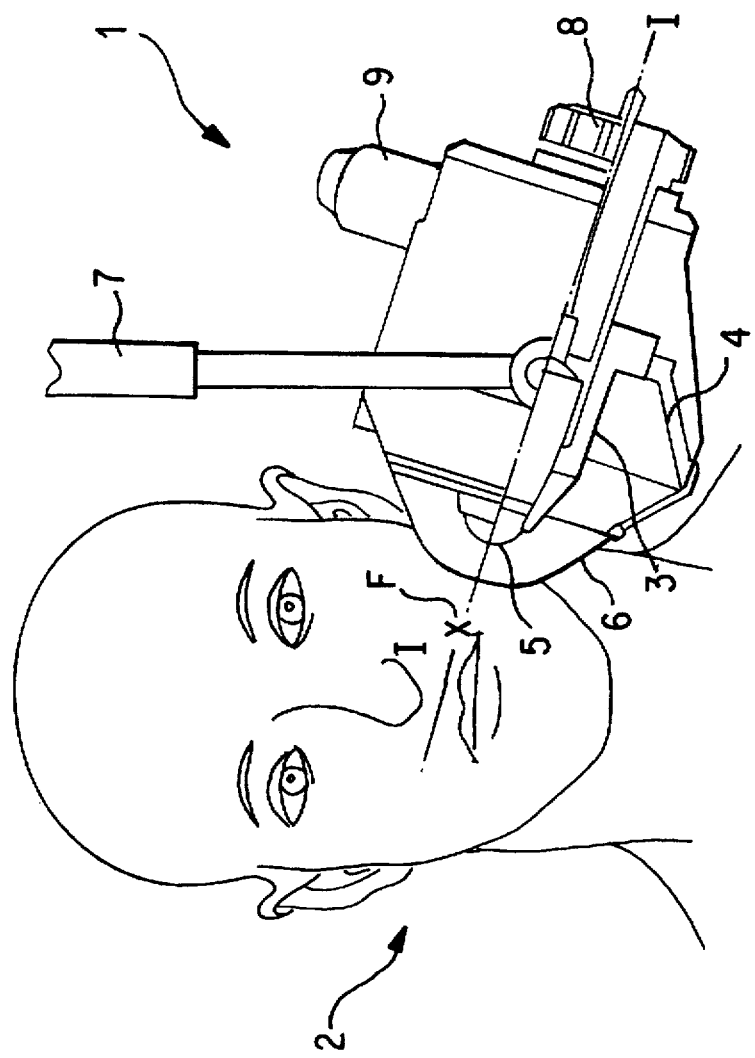

FIG. 1 shows an apparatus for treating teeth indicated in general by reference numeral 1. The stylized head of a person to be treated is indicated by reference number 2.

The apparatus 1, shown in an external view above line I—I and with its housing 1' shown "cut away" below line I—I, has a sound generating unit which generates focused acoustic pressure or sound waves and is constructed according to the teaching of German Patent document DE 38 35 318 C1.

In particular, the sound generator 3 of the sound generating unit has the shape of a cylinder which radiates sound waves by means of its cylindrical surface. A reflector 4, which surrounds the sound generator 3 and, in particular, has the shape of a paraboloid of rotation, reflects the sound waves radiated radially outward by the sound generator 3 so that they are focused in a small area around a focal point F.

The sound generator 3 can have an electromagnetic, magnetostrictive, or piezoelectric pressure wave generator or a shock wave unit with electrodes, or an explosive unit.

An aiming unit 5 is disposed inside the sound generator. The aiming unit 5 can, for example, be an x-ray unit mounted so as to be displacable along axis I—I. At its end facing the person 2 to be treated, the apparatus 1 is closed-off by a cushion 6 which seals the inside of the apparatus in a fluid-tight manner and abuts the person's cheek adjacent to the tooth to be treated.

The apparatus 1 is mounted to a support 7 so as to be pivotable about an axis perpendicular to axis I—I such that it can be positioned relative to the head of the person 2 according to the location of the tooth to be treated. For this purpose, in the embodiment shown, support 7 is designed as a telescoping arm which can be rotated or pivoted additionally about at least two axes.

Reference number 8 designates a connector for aiming unit 5, and reference number 9 designates a connector for the sound generator 3, by means of which the latter is connected with a control unit, not shown.

With the device shown in FIG. 1, it is possible for example, for removing tooth fillings, to couple-in focused acoustic pressure or shock waves with appropriate energy into the tooth and/or the filling.

By means of the shock or pressure waves coupled into the tooth or filling, the connection between the filling and the tooth is destroyed, so that in most cases the filling can be removed as a whole. However, even when the filling is destroyed, the resulting fragments are so large that they can be easily removed or suctioned-off without dust developing and without the risk of the patient swallowing the fragments.

If the device shown is operated such that it emits focused acoustic pressure or shock waves with a higher energy than in the case of filling removal, the teeth can be advantageously shattered by it. This facilitates extraction of teeth, particularly wisdom teeth, since the fragments, for example the parts of a split tooth, can be removed more easily and less "bloodily" than a tooth as a whole.

The present invention has been described above on the basis of one embodiment. Of course, widely varying forms are possible and will be readily recognizable to one of ordinary skill in the art.

Thus, in addition to cushion 6, an additional coupling cushion can be provided (FIG. 1A). The additional coupling cushion couples-in the focused waves through the cheek and/or the open mouth into the tooth or filling to be removed. The additional cushion can be disposed between the cheek and the tooth.

Since as a rule, both cushion 6 and the additional cushion are filled with a fluid, for example water, which must be degassed in order not to disturb the propagation of the ultrasonic waves, it is preferable for the additional cushion to be connected in fluid fashion with the coupling cushion 6, so that degassing of the fluid is ensured in the additional cushion.

The device for generating sound or pressure waves can be designed such that it can be introduced into the mouth of the person to be treated. In this connection, it is possible to have cushion 6 directly abut the tooth to be treated.

The pressure wave generator or shock wave unit can also be designed in a different manner from the embodiment shown without departing from the spirit and scope of the invention.

For example, the pressure wave generator or shock wave unit can have the shape of a dome, so that even without an additional focusing unit, such as an acoustic lens for example, focused waves are generated.

This possibility is of course not limiting, as all the possibilities for sound generation known from the literature can be used. The possibility shown in the drawing is preferred, however.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for removing tooth fillings, the method comprising the steps of:

generating one of focussed acoustic pressure and shock waves at an appropriate energy level; and coupling said generated focussed waves into at least one of a tooth and tooth filling to loosen said tooth filling, wherein said step of coupling said generated focussed waves is performed by coupling-in said generated focussed waves through a cheek of a patient.

2. The method according to claim 1, further comprising arranging a coupling cushion between the cheek and the tooth prior to coupling said generated focussed waves.

3. A method for shattering a tooth, the method comprising the steps of:

generating one of focussed acoustic pressure and shock waves at an appropriate energy level; and coupling said generated focussed waves into the tooth to shatter the tooth, wherein said step of coupling said generated focussed waves is performed by coupling-in said generated focussed waves through a cheek of a patient.

4. The method according to claim 3, wherein said tooth is a wisdom tooth.

5. The method according to claim 3, further comprising arranging a coupling cushion between the cheek and the tooth prior to coupling said generated focussed waves.

* * * * *